(12) United States Patent
Muller et al.

(10) Patent No.: US 10,682,039 B2
(45) Date of Patent: Jun. 16, 2020

(54) VIDEO ENDOSCOPIC DEVICE

(71) Applicant: Xion GmbH, Berlin (DE)

(72) Inventors: Holger Muller, Glienicke-Nordbahn (DE); Alexander Kliem, Berlin (DE)

(73) Assignee: XION GMBH (DE)

( * ) Notice: Subject to any disclaimer, the term of this patent is extended or adjusted under 35 U.S.C. 154(b) by 216 days.

(21) Appl. No.: 14/285,107

(22) Filed: May 22, 2014

(65) Prior Publication Data

US 2014/0357951 A1 Dec. 4, 2014

(30) Foreign Application Priority Data

May 28, 2013 (DE) .......................... 10 2013 209 956

(51) Int. Cl.
| | | |
|---|---|---|
| *A61B 1/00* | (2006.01) | |
| *G02B 23/24* | (2006.01) | |
| *H04N 13/218* | (2018.01) | |
| *A61B 1/055* | (2006.01) | |
| *A61B 1/06* | (2006.01) | |
| *H04N 5/225* | (2006.01) | |

(52) U.S. Cl.
CPC ...... *A61B 1/00009* (2013.01); *A61B 1/00045* (2013.01); *A61B 1/055* (2013.01); *A61B 1/06* (2013.01); *G02B 23/2415* (2013.01); *G02B 23/2446* (2013.01); *H04N 13/218* (2018.05); *H04N 2005/2255* (2013.01)

(58) Field of Classification Search
CPC . A61B 1/00193; A61B 1/002; A61B 1/00105; A61B 1/00057; A61B 1/00059; A61B 1/042; A61B 1/055; G02B 23/2415; G02B 23/2446

USPC ......................................... 600/133, 136, 172
See application file for complete search history.

(56) References Cited

U.S. PATENT DOCUMENTS

| | | |
|---|---|---|
| 3,257,902 A | 6/1966 | Hopkins |
| 4,651,201 A | 3/1987 | Schoolman |
| | (Continued) | |

FOREIGN PATENT DOCUMENTS

| | | |
|---|---|---|
| DE | 9200876 U1 | 4/1993 |
| DE | 4405102 A1 | 8/1994 |
| | (Continued) | |

*Primary Examiner* — Alexandra L Newton
(74) *Attorney, Agent, or Firm* — Ware, Fressola, Maguire & Barber LLP

(57) ABSTRACT

A video endoscopic device has a camera head and two parallel optical arrangements, each with optical components, arranged coaxially with one another along a common first optical axis of the optical components of a respective optical arrangement and in the interior of an endoscope shaft. The optical components transmit an optical image from a distal end of the respective optical arrangement to a proximal end of the respective optical arrangement. The camera head contains at least one image sensor comprising a recording plane and at least two projection objectives, each having a second optical axis and arranged to project an image onto the image sensor. The optical arrangements comprise a collimating optical unit for generating an at least approximately parallel beam path at the outlet of the respective optical arrangement. The respective collimating optical unit has a third optical axis arranged coaxially with the optical components of the optical arrangements.

15 Claims, 11 Drawing Sheets

(56) References Cited

U.S. PATENT DOCUMENTS

| | | | |
|---|---|---|---|
| 4,781,448 A | 11/1988 | Chatenever et al. | |
| 4,862,873 A | 9/1989 | Yajima et al. | |
| 5,295,477 A | 3/1994 | Janfaza | |
| 5,459,605 A * | 10/1995 | Kempf | A61B 1/00165 359/462 |
| 5,527,263 A | 6/1996 | Zobel et al. | |
| 5,588,948 A * | 12/1996 | Takahashi | A61B 1/00179 348/45 |
| 5,751,341 A | 5/1998 | Chaleki et al. | |
| 5,771,991 A | 6/1998 | Fresco | |
| 5,776,049 A | 7/1998 | Takahashi | |
| 5,861,987 A | 1/1999 | Nakamura et al. | |
| 6,088,157 A * | 7/2000 | Mazurkewitz | A61B 1/002 359/434 |
| 6,108,130 A | 8/2000 | Raj | |
| 6,113,533 A | 9/2000 | Howes et al. | |
| 6,139,490 A | 10/2000 | Breidenthal et al. | |
| 6,582,358 B2 | 6/2003 | Akui et al. | |
| 7,671,888 B2 | 3/2010 | Nogami et al. | |
| 2001/0012053 A1* | 8/2001 | Nakamura | A61B 1/00193 348/45 |
| 2003/0125608 A1* | 7/2003 | Igarashi | A61B 1/00096 600/166 |
| 2006/0041187 A1* | 2/2006 | Rudischhauser | A61B 1/00163 600/138 |
| 2011/0043612 A1* | 2/2011 | Keller | A61B 1/00165 348/49 |
| 2012/0130252 A1 | 5/2012 | Pohjanen et al. | |
| 2014/0177043 A1* | 6/2014 | Togino | A61B 1/00193 359/367 |
| 2014/0343362 A1* | 11/2014 | Tesar | A61B 1/002 600/181 |

FOREIGN PATENT DOCUMENTS

| | | |
|---|---|---|
| DE | 197 42 454 A1 | 4/1999 |
| DE | 69627497 T2 | 12/2003 |
| JP | H0659196 A | 3/1994 |
| JP | 2001147382 A | 5/2001 |
| JP | 2003061905 A | 3/2003 |
| RU | 2483469 C2 | 5/2013 |
| WO | 95/12345 | 5/1995 |
| WO | 2011/014687 A2 | 2/2011 |

\* cited by examiner

VIDEO ENDOSCOPIC DEVICE

CROSS REFERENCE TO RELATED APPLICATION

This application claims priority under 35 USC § 119 to German Patent Application No. 102013209956.8 filed on May 28, 2013, which application is hereby incorporated by reference in its entirety.

TECHNICAL FIELD

The invention relates to a video endoscopic device, comprising an endoscope shaft and a camera head, in which two separate stereoscopic partial images are projected onto a common image sensor or two image sensors. These partial images can be converted into a stereoscopic image by means of an image processor and depicted on a stereoscopic screen.

BACKGROUND OF THE INVENTION

Conventionally, stereoscopic surgical microscopes are used during surgery. In minimally invasive surgery, these instruments cannot be used and the operating medical practitioner can observe the operating site situated in a body opening only by means of an endoscope or other special aids. When performing such operations, stereo endoscopes provide additional depth information compared to conventional mono-endoscopes. Stereoscopic video endoscopes moreover enable image observation on a screen or on multiple screens and the storage of videos.

A stereoscopic video endoscope can be designed according to the principle of the rigid endoscope with two parallel beam paths. Here, two objectives arranged next to one another generate two intermediate images, which depict an object situated in front of the endoscope from different viewing angles. There is image transmission to the proximal end of the endoscope shaft by means of two parallel transmission optical units. There, images can be projected onto one or more image sensors, such as e.g. CCD- or CMOS-type image sensors.

U.S. Pat. No. 5,295,477 discloses a rigid stereo endoscope and a tube-like stereo endoscope made out of collar elements. The endoscope contains a guide or lenses in order to transmit an optical image from the end of the endoscope to a microscope connected to the endoscope. An optical waveguide contained in the endoscope transmits light from a light source into a biological specimen. A movable prism is attached to the end of the endoscope.

U.S. Pat. No. 5,527,263 discloses a rigid visual stereo endoscope with rod lenses. The endoscope contains two deflection prism pairs comprising a respective first prism coaxially with the respective optical system and a respective second prism which re-aligns the viewing axis in parallel with the optical axis. Transparent protection elements are arranged in the beam paths.

U.S. Pat. No. 4,651,201 combines a stereo endoscope containing rigid rod lenses with two cameras. The cameras transmit two stereoscopic images to two screens which are attached to a head-worn implement in front of the eyes of the user.

U.S. Pat. No. 4,862,873 discloses a video endoscope containing rigid rod lenses, comprising two image sensors, which contains an optical waveguide and an image guide. A stereoscopic image is generated by a change in the functions of the guides.

A rigid stereoscopic video endoscope with rod lens systems for image transmission is disclosed in U.S. Pat. No. 5,577,991. The video endoscope contains two parallel beam paths, in which there is image transmission by means of rod lens systems. At the proximal end of the endoscope shaft, plane mirrors direct the respective beam onto two image sensors. At the proximal end of the optical arrangement, a visual field stop is attached in the respective beam path. The visual field stops and plane mirrors can be adjusted in order to set the position of the images on the screen.

U.S. Pat. No. 6,139,490 discloses a stereo endoscope and virtual reality glasses which can be connected therewith.

U.S. Pat. No. 5,751,341 discloses a stereo endoscope comprising a plurality of shaft parts, as a result of which the shaft is rotatable.

U.S. Pat. No. 6,108,130 discloses a stereoscopic lens system and a stereoscopic image sensor with a pair of fields. A reduced distance between the images on the image sensor is obtained by an image redirection of the image information by means of the gradient lens from the image collection systems to the fields of the image sensor.

U.S. Pat. No. 6,582,358 discloses a stereo endoscope with a third beam path. The third beam path contains an optical device with a larger viewing angle than the optical devices used for stereoscopy.

U.S. Pat. No. 7,671,888 discloses a stereo endoscopic screen control device with a masking system.

U.S. Pat. No. 5,776,049 discloses a stereo endoscope with an adjustment control loop.

WO 2011/014687 A2 discloses a stereoscopic video endoscope with parallel image transmission. The image is obtained through light openings at the distal end of an endoscope shaft and transmitted in two stereoscopic partial images through the endoscope shaft to one or two outlet optical units, which project the image onto an image sensor of a camera.

The basic design of a rigid monoscopic endoscope with rod lenses emerges from the patent document U.S. Pat. No. 3,257,902. In an elongate tube, an objective and rod lens systems are arranged in succession along a common optical axis. The rod lenses serve for image guidance to the proximal end of the tube. An eyepiece, which generates a virtual image visible to the human eye, is arranged behind the proximal end of the tube. The image generated by the eyepiece can also be recorded by a suitable camera.

SUMMARY OF THE INVENTION

The invention is based on the object of developing a stereoscopic video endoscope, according to the principle of the rigid endoscope with two parallel beam paths and rod lens systems for image guidance, in such a way that adjustment-sensitive components are avoided and simple production is made possible. Convenient handling of the endoscope and use of high-resolution image sensors are to be made possible in the case of a small diameter of the endoscope shaft.

According to the invention, this is achieved by a video endoscopic device comprising two parallel optical arrangements, which, together, are arranged at least in part in the interior of an endoscope shaft, and a camera head arranged adjacent to or adjoining the proximal ends of the optical arrangements. The optical arrangements each comprise optical components, arranged coaxially with one another along a respective common first optical axis of the optical components of a respective optical arrangement. Each optical arrangement is configured to transmit an optical image from a distal end of the respective optical arrangement to a proximal end of the respective optical arrangement. The camera head comprises at least one image sensor comprising at least one recording plane and at least two projection objectives. By way of example, the image sensor can be a CCD colour sensor, a CMOS colour sensor or the like. Here, each one of the projection objectives has a respective second optical axis and is arranged and configured to project an image onto the image sensor. The optical arrangements each comprise a collimating optical unit, arranged at the respective proximal end thereof, for generating an at least approximately parallel beam path at the outlet of the respective optical arrangement. The collimating optical unit has a third optical axis that is arranged coaxially with the optical components of the optical arrangement or laterally offset by at most half a diameter of the collimating optical unit from the respective common first optical axis of the optical components of the optical arrangement. Each one of the at least two projection objectives is arranged and configured to image the parallel beam path, generated by a respective collimating optical unit, on at least one focus in the at least one recording plane of the at least one image sensor. At least one of the projection objectives is arranged so that the respective second optical axis has a lateral distance, measuring at most half a diameter of the projection objective, from the respective third optical axis of the collimating optical unit which generates the parallel beam path, the projection objective being arranged and configured for imaging said parallel beam path on the at least one focus. As result of this, the parallel beam path enters the at least one projection objective with a lateral distance from the second optical axis of the at least one projection objective. The latter means that a central ray propagating along the third optical axis of the collimating optical unit enters the projection objective with a lateral offset to the second optical axis thereof.

In this text, the optical axis should be understood to mean that straight line which corresponds to the axis of symmetry of an optical component. Furthermore, the common optical axis of an arrangement of optical components is to be understood to mean that line which is formed by the optical axis of the individual optical components. This means the common first optical axis elongates along the optical axes of each of the optical components of each one of the two parallel optical arrangements. Each second optical axis elongates along each one objective and the third optical axis elongates along each one collimating optical unit. The third optical axis is aligned with the first optical axis of one of the two parallel optical arrangements, when the collimating optical unit is arranged coaxially with the optical components of the optical arrangement such that the third optical axis forms part of the first optical axis.

Each one of the parallel optical arrangements transmits an image—a so-called stereoscopic partial image—from the distal end of the optical arrangement to the proximal end of the optical arrangement. A collimating optical unit, which generates a parallel beam path, is arranged at the distal end of the optical arrangement. Each one of the parallel beam paths containing the stereoscopic partial image is incident on a projection objective and enters the latter with a lateral distance from the second optical axis of the projection objective. As a result of this, the two stereoscopic partial images are deflected in such a way with respect to one another that the lateral distance between the two stereoscopic partial images is modified. By way of example, if the lateral distance between the two stereoscopic partial images is increased, this renders it possible to separate the stereoscopic partial images so far from one another that they can be imaged on the recording plane of the image sensor in such a way that the two stereoscopic partial images can be output as a stereoscopic image signal on a stereoscopic screen. The respective stereoscopic partial image corresponds to a view of an object, for example a cavity, an organ, parts thereof or a combination thereof, situated in an object plane. The two stereoscopic partial images are brought together by the video endoscopic device in such a way that a stereoscopic image, which imparts a spatial impression with depth information of the object observed with the video endoscopic device, is generated.

Here, an endoscope or stereo endoscope is to be understood to mean the endoscope shaft with all optical components comprised by the endoscope shaft.

An advantage of the invention is that the usual adaptation at size and location of the outlet pupil to the human eye with respect to the eyepieces used in the prior art is dispensed with. By way of example, the collimation can be achieved by rod lenses or rod lens systems at the light outlet of the elongate shaft of the stereo endoscope. Furthermore, compared to other lens systems, an advantage offered by rod lenses or rod lens system is that the transmission of a substantially brighter image with higher image quality is made possible. The assembly in the endoscope shaft is also simplified due to the elongate geometry of the rod lenses. The arrangement of two parallel beam paths extending closely next to one another is also possible for small shaft diameters. A deterioration in the image quality at the edge can also be avoided well. It is possible to correct the off-axis image aberrations such as coma and astigmatism by means of the video endoscopic device according to the invention. A further advantage of the invention consists of the fact that a lateral distance between the stereoscopic partial images in the recording plane can be set virtually arbitrarily, even if the distance between the stereoscopic partial images is very small in the objectives at the distal end. As a result, it is possible to construct a versatile stereo endoscopic system. In accordance with a respective medical application, a respective camera head can be connected to different interchangeable endoscopes, each with a different stereoscopic base length. Moreover, the optical system according to the invention has a lower sensitivity towards tolerances. As a result of this, the demands on the mechanical accuracy of a connection of the camera head are reduced compared to stereo endoscopes from the prior art.

In a preferred configuration, the optical arrangements are arranged in a rigid endoscope shaft; in this case, the optical components arranged coaxially with one another are arranged along a longitudinal axis of the endoscope shaft. Alternatively, the endoscope shaft can also have a flexible configuration, for example as a tube, as a collar-surrounded tube or the like. For a flexible endoscope shaft, the optical components arranged coaxially with one another are arranged along the rigid straight longitudinal axis of the endoscope shaft in a rigid straight state of the endoscope shaft. By generating curvature along the endoscope shaft, for example by insertion into a lumen and bending of the endoscope shaft, the optical components are displaced in accordance with the curvature of the endoscope shaft.

The at least approximately parallel beam path at the outlet of the respective optical arrangement can have a deviation from the ideal collimation of up to +/−10 dioptre without this impairing the stereoscopic display. Both the beam path from each one of the collimating optical units and the beam paths of the collimating optical units may be only approximately and not completely parallel to one another, i.e. have a deviation, for example due to manufacturing tolerances. By way of example, the resulting tolerance in the collimation between the left-hand and right-hand beam path can be compensated for when focusing the camera head. Alternatively or additionally, there can also be tuning of the collimation of both approximately parallel beam paths by adjusting the axial distances between two or more optical components, e.g. rod lens systems.

The optical components arranged coaxially with one another are preferably rod lens systems. The rod lens systems may be rod lenses cemented to one another. It is also feasible to cement rod lenses with other lenses for producing a rod lens system. The optical components arranged coaxially with one another can also be rod lenses. Alternatively or additionally, the optical components may have other lenses or optical elements.

In a preferred configuration, all optical components of the optical arrangement, the collimating optical unit, the objectives and the projection objectives or a projection optical unit have the same external diameter, as a result of which there is a simpler mechanical design for the endoscope. Two parallel tubes, the internal diameter of which can be selected to match the external diameter of the optical components, objectives and collimating optical unit, can be arranged in the interior of the endoscope shaft, as a result of which the objective and the optical components for image guidance and collimation can be arranged in each one of these tubes according to the principle of the filling holder. The axial distances between the optical components, if present, can be filled by a gas mixture, a gas, a liquid, a solid or a different filling medium. Preferably, this is a gas mixture or a gas, which is delimited by spacer tubes arranged axially between the optical components. The optical characteristics of the filling medium can be optimized for the optical components or the beam path produced thereby. The tubes formed by spacer tubes and optical components moreover support the centering of the two parallel beam paths arranged in the shaft, as a result of which further components, for example light sources, optical waveguides, work channels for surgical operating tools or for transporting fluids, or the like, can be arranged in the interior of the endoscope shaft, parallel to the two tubes. In a further configuration, the two tubes can also be unified to form a common component with two parallel cylindrical passage holes for holding the optical components.

The video endoscopic device can have one or more mechanical interfaces for releasable or permanent attachment of the video endoscopic device to stand systems, robot arms, trocars, sleeves or the like. The mechanical interface or interfaces can be arranged e.g. on the endoscope shaft, on other components or component parts of the endoscope and/or on the camera head. Such mechanical interfaces are known to a person skilled in the art from the prior art. By way of example, these include bayonet connectors, screw-in connections, clamping connections with a spring release or the like.

The collimating optical units for generating an at least approximately parallel beam path at the outlet of the optical arrangements are preferably rod lens systems, which comprise cemented rod lenses and/or other lenses. A rod lens system preferably contains a rod lens cemented to other lenses. The collimating optical units can also be rod lenses.

The collimating optical units, preferably rod lens systems or rod lenses, can be designed according to a design conventional for endoscopic image guidance systems. Preferably, the rod lens systems for the purposes of collimation are of the same design as rod lens systems employed for image transmission. In this context, of the same design may mean that the image guiding and collimating rod lens systems for example each have two plano-convex lenses and a rod lens cemented to these, i.e. the rod lens system contains an equal number of different lenses for collimating and image guiding rod lens systems. The dimensions, such as e.g. diameter, focal lengths or the like, of the rod lens systems of the same design can be selected to be different from one another for the image guiding and collimating rod lens systems. The rod lenses for collimation and image transmission can have dimensions identical to one another or dimensions different from one another. In a preferred configuration, the at least two projection objectives are respectively arranged such that the second optical axis is arranged offset laterally by at most half a diameter of the respective projection objective to the respective optical axis of the respective optical component.

In a preferred configuration, at least one of the parallel optical arrangements comprises a resilience element arranged between two successive optical components. It is also possible for both parallel optical arrangements to comprise one or more resilience elements, for example between all successive optical components, such that one or more resilience elements are arranged in each case between two optical components. The respective resilience element may be a gas mixture, a gas, a liquid, a solid or a different type of resilience element which is situated in the axial distance between the two successive optical components. It is also possible to combine two resilience elements, for example a gas and a solid. Preferably, the resilience element is a solid in the form of a mechanical spring. By way of example, the mechanical spring can be arranged in a gas or a liquid which can be situated as a further resilience element in the axial distance between the two successive optical components. The resilience element is preferably configured to ensure an axial distance between the two successive optical components such that mechanical play between the optical components is reduced or prevented. Here, mechanical play is prevented or at least reduced by the spring action of the resilience element.

In a particularly preferred configuration, the resilience element is arranged between an optical component, arranged closest to the collimating optical unit, of the at least one of the parallel optical arrangements and the collimating optical unit. In this case, the collimating optical unit is preferably a collimating rod lens system.

The axial freedom of movement of the optical component arranged closest to the proximal end of the parallel optical arrangement, for example the collimating optical unit in the form of a collimating rod lens system, is preferably restricted by a termination cap in the direction of the spring effect. The termination cap can also enclose the collimating optical unit. The termination cap preferably has a cylindrical external surface with a one-sided flattening along a longitudinal axis of the termination cap such that a flattened or cut cylindrical shape, which does not completely extend around the circular circumference, is generated. The termination cap can have a projection at a termination cap end, which projection reduces an internal diameter of the termination cap at the termination cap end so as to restrict the axial freedom of movement of the collimating optical unit. To this end, the projection preferably extending along the termination cap end in circular form serves to restrict a movement of the collimating optical unit at the proximal end of the parallel optical arrangement. Alternatively or additionally, the collimating optical unit can also be fastened permanently, for example adhesively bonded, to the termination cap and/or the termination cap end.

In a preferred configuration, the video endoscopic device comprises a holding device at the proximal end of the parallel optical arrangements. The holding device is preferably configured to hold the collimating optical units of the parallel optical arrangements in such a way that, in a locked state of the holding device, an axial and/or lateral movement of the collimating optical units is prevented. By way of example, the holding device can be configured in the form of a clamping device, which surrounds the collimating optical units or the termination caps surrounding the collimating optical units and exerts a pressure force on the latter such that an axial and/or lateral movement is prevented or reduced. The holding device can comprise one or more setting units, for example set screws, which can be adjusted continuously so as to set a pressure force which prevents the movement of the parallel optical arrangements. If the setting unit sets the holding device in a holding state or a locked state, the proximal ends of the parallel optical arrangements or the termination cap ends are held at a fixed axial distance from the tubes surrounding the parallel optical arrangements. In a loosened or an open state of the holding device, it is possible to set the axial distance between the proximal ends of the parallel optical arrangements, or the termination cap ends, and the tubes in which the parallel optical arrangements are arranged. In a particularly preferred configuration of the holding device, the holding device comprises a slotted block with a set screw and a slot for holding the termination caps. If there is a sufficient distance between the two parallel optical arrangements, the video endoscopic device can also comprise two separate parallel optical arrangements in two round holes with a slot and separate holding devices.

The termination cap preferably comprises an optical window transparent to visible radiation or light, or a radiation-transmissive opening. The termination cap can be hermetically sealed with the aid of a seal, as a result of which the parallel optical arrangements can also be hermetically sealed. Preferably, the proximal end of the parallel optical arrangements is hermetically sealed by the termination cap with the optical window. To this end, the termination cap can also be surrounded by a protective cap. In one configuration, the protective cap is configured to be screwed onto the termination cap or the termination caps which surround the proximal end of the parallel optical arrangements.

One aspect of the configuration of the invention with a resilience element is that the video endoscopic device is neither damaged nor defocussed or decollimated in the case of thermal expansion, such as, for example, during vapour sterilization. At the same time, the configuration of the invention renders an adjustment of focus and/or collimation possible during the production of the video endoscopic device, which adjustment enables a sufficient correspondence of the image locations of the two parallel optical arrangements in order to generate a stereoscopic image.

In a preferred configuration, the endoscope shaft contains an illumination device for illuminating an object plane and/or said endoscope shaft is connected to an illumination device. Light from a light source can be transmitted in an optical waveguide from the proximal shaft end via an illumination-light inlet arranged in the vicinity of, or at, the proximal end of the endoscope shaft to an illumination-light outlet arranged in the vicinity of, or at, the distal end of the endoscope shaft in order to illuminate an object. It is also possible to transmit the light from a plurality of light sources. The light source can be contained in the camera head and/or connected to the endoscope shaft in either a releasable and re-lockable or rigid manner by a flexible optical waveguide, for example an optical fibre cable or the like.

Preferably, the video endoscopic device contains an image processor which can convert two stereoscopic partial images projected onto the image sensor into an image signal which can be displayed on stereoscopic screens. The image processor can be arranged within or outside of the video endoscopic device and comprise electronic components and/or software components. Moreover, stereoscopic partial images projected onto a plurality of image sensors can also be converted by the image processor or processors into image signals which can be depicted on stereoscopic screens and these image signals can be output on stereoscopic screens, for example on screens based on the polarization-glasses principle, on screens based on the shutter-glasses principle or the like. The image processor can preferably perform image-improving measures, for example adaptation of contrast, colour display, improvements in the focus, correction of distortion, image-position deviations, instances of masking, adaptation of the stereoscopic vergence and/or compensation of tolerances in the image scale, by means of image processing.

The components, for example camera head, projection objective, endoscope shaft, optical components and/or optical arrangements, may be interchangeable. By way of example, a projection objective in or on a camera head may be replaced by a different projection objective or by a plurality of projection objectives. It is also possible to interchange the whole camera head. It is also possible to interchange an endoscope shaft with the optical components contained therein. It is also possible only to interchange individual optical components of the endoscope arranged in the endoscope shaft, in particular the collimating optical unit. To this end, the interchangeable components are preferably connected to one another in a releasable and re-lockable manner, for example by mechanical coupling, as a result of which the sterilization of the components of the video endoscopic device is simplified. The newly connected components can be calibrated with respect to one another.

In a preferred configuration, the video endoscopic device contains a memory unit which can contain, for example, a stored set of predetermined calibration data. The calibration data can be saved in an unchanging manner in unwritable memory and/or the calibration data can be saved in writable memory by calibration at any time. Here, a calibration iteration can be used to produce a set of new calibration data, which can be saved in the memory unit. The memory unit can also contain and/or save other data, e.g. history data about the use of the endoscope and/or the light source, in order to establish when it is necessary to renew the device and/or light source, or data from sensors, for example temperature sensors, hygrometer sensors or the like, which can be used for calibration. The calibration data from the memory unit of the video endoscopic device can particularly preferably be used to calibrate newly connected components with respect to one another by a saved set of predetermined calibration data. Here, the calibration data can originate in a pre-saved manner from the factory or can be generated in a calibration iteration, as a result of which an individual selection of the employed components in an endoscope is possible without having to carry out a new calibration during each use. Moreover, the video endoscopic device can comprise one or more sensor devices, e.g. RFID transceivers, which can read and process readable markings, e.g. RFID transponders or the like, on the components. As a result of this, calibration data may be loaded automatically. To this end, the sensor devices can identify the respective connected components on the basis of their sensor-readable marking and select, from the saved calibration data the calibration data, or the calibration data with the best fit for the newly connected components and calibrate the video endoscopic device using these calibration data. The sensor device is preferably on or in the camera head.

The video endoscopic device can contain one or more transparent protective windows which are provided for protection against environmental influences. By way of example, the protective windows can be arranged at the distal end of the endoscope shaft for protecting the objectives, in the endoscope shaft, at the proximal end of the endoscope shaft for protecting the collimating optical unit, on the light inlet of the projection objective or on the light inlet of the camera head for protecting the projection objectives and/or between projection objectives and image sensor for protecting the image sensor.

In a further configuration, the video endoscopic device can comprise one or more visual field stops. The visual field stops are preferably arranged in or at the proximal end of one or both parallel optical arrangements in order to block and/or limit one or both beam paths of the parallel optical arrangement in a temporary or permanent manner.

The camera head of the video endoscopic device can comprise a focusing device. The focusing device can be operated manually by a user or automatically by means of a control loop or by means of a program or a piece of software running on a computer or the like. The focusing device can enable focusing of the images of the image signal by virtue of the focusing device shifting the projection objective or the projection objectives, which may have a fixed or variable focal length, or components of the projection objective or of the projection objectives in the axial direction. In particular, a left-hand and a right-hand stereoscopic partial image can be focussed independently from one another by the focusing device. The partial images generated in the plane of the image sensors can overlap in part without the stereoscopic display being impaired as long as the overlap does not capture the regions detected in the image of the image signal. Moreover, the partial images can be focussed on different image sensors or on one image sensor.

The camera head can be connected to the endoscope, in particular to the endoscope shaft, via a releasable and re-lockable coupling. The releasable and re-lockable coupling can use locking mechanisms known from the prior art, for example in the form of a screw-in connection, a self-triggering spring mechanism, a clamping jaw, an eccentric tappet or the like. The endoscope shaft and the camera head can have coupling surfaces matched to one another such that a coupling half of the endoscope shaft can be inserted in an interlocking manner into a coupling half of the camera head. The coupling surfaces can be configured to prevent rotation between the endoscope shaft and the camera head. To this end, the coupling surfaces can have corresponding anti-rotation device elements, for example slots, bolts, pins or the like. A number of solutions of such anti-rotation devices are known to a person skilled in the art from the prior art. The anti-rotation device elements can be configured in such a way that they only allow a restricted number of configurations of the camera head relative to the endoscope shaft, for example only a fixed configuration, two configurations rotated by a rotation angle of 180°, or similar configurations. The anti-rotation device elements render it possible to prevent unwanted relative rotation of camera head and endoscope shaft.

Anti-rotation couplings for the releasable and re-lockable coupling of stereo endoscopes with stereoscopic camera heads are known from e.g. the German utility model G 93 00 529.6. In this application, dowel pegs and holes are shown for the repeatable axial alignment between the two light outlets of the stereo endoscope and the two light inlets of the camera head.

The endoscope shaft and the camera head are preferably connected to one another via the coupling in such a way that a stereoscopic horizon of the endoscope is aligned substantially parallel to the horizontal lines on the image sensor or the image sensors of the camera head. Alternatively, the stereoscopic partial images can be rotated into the correct orientation by the image processor.

Furthermore, the endoscope shaft is preferably arranged relative to the camera head in such a way that a horizontal connection line between the two projection objectives is arranged substantially parallel to the stereoscopic horizon of the endoscope. However, a precise axial alignment between the respective collimating optical unit and the respective projection objective is not mandatory due to the low tolerance sensitivity of the invention.

Lateral changes in the focal points in the recording plane of the stereoscopic partial images, resulting from mechanical play, tolerances or the like, can be compensated for by the image processor or imaging electronics.

As a result of the low tolerance sensitivity of the video endoscopic device, the mechanical design of the camera head is simple and can be brought about analogously to a mechanical design in the case of known microscopic endoscopy systems. To this end, several solutions are known from the prior art, which can be transferred to the mechanical design of the camera head of the video endoscopic device in an obvious manner.

Examples of such mechanisms for commercially available camera heads are described in U.S. Pat. Nos. 4,781,448 and 6,113,533. In the sleeve structure described therein, the coupling can be combined with an operating element for manual or electric motor-driven focusing of the projection objectives which are arranged to be movable in the longitudinal direction in the camera head. Here, a cylindrical objective carrier, which has a pin or bolt as pickup and anti-rotation device for the projection optical unit, is guided within a fixed external cylindrical sleeve. In the case of a rotational movement of an outer focusing sleeve provided with a helical groove, there is a translational focusing movement of the objective carrier. Transparent protective windows or optical filters can be arranged in the vicinity of the distal and proximal end of the sleeve. The coupling is arranged at the distal end of the fixed sleeve.

It is also possible to arrange two parallel projection objectives in such an objective carrier. By way of example, the holder for the projection objectives can be realized by two bores which are parallel to one another and horizontally offset from one another. Such a stereoscopic adapter with common focusing of the projection objectives in the coupling adapter is known from e.g. U.S. Pat. No. 6,582,358. Both stereoscopic partial images can be focussed together by rotating the focusing ring. During the assembly, the projection objectives are preferably set to a common focus location along the axis thereof.

The illumination device can also be designed analogously to a monoscopic endoscopy system. The radiation source, preferably a light source, can be arranged e.g. in and/or on the endoscope or in and/or on the camera head. The endoscope shaft can comprise optical waveguides which are configured to transmit the light generated by the light source to the distal end of the endoscope shaft. By way of example, the optical waveguide or optical waveguides can comprise glass cones, optical fibre cones, lenses, mirrors or the like for beam shaping.

Alternatively or additionally, a light inlet can also be arranged at the coupling site between endoscope shaft and camera head such that an optical connection of the illumination device is also established when coupling an endoscope to a camera head.

One aspect of a configuration of the video endoscopic device according to the invention is that, in the endoscope shaft, a large cross section can be filled with optical waveguides, for example optical fibres. Optical waveguides which largely fill the cross section of the endoscope shaft can be arranged in the endoscope shaft. Only the cross section assumed by the tubes which comprise the parallel optical arrangements used for image guidance is not available for optical waveguides.

In a further configuration, prisms behind or in the projection objectives can generate a directional change of the objective beam paths, wherein, as a result of this, the viewing direction of the video endoscopic device is not parallel to the axis of the endoscope shaft and therefore also not parallel to the respective optical axis of the respective arrangement of the optical components. The viewing direction can be re-oriented parallel to the axis by means of further prisms arranged in the beam path. The prisms or the respective prism can be an achromatic prism or a reflection prism; alternatively, it is also possible to use a mirror arrangement with an angular deflection of less than 30°. It is also possible to arrange a plurality of prisms and/or mirror arrangements in parallel and/or in series. In a preferred configuration, the prisms or mirror arrangements are cemented to other optical components. By way of example, the prisms can be cemented to other prisms, lenses or other optical elements.

The distal end of the endoscope shaft can also be angled. Moreover, objectives with lateral viewing direction, arranged at the distal end of the endoscope shaft can be used, as result of which it is possible to obtain a stereo endoscope in which the viewing direction is at an angle to the axis of the endoscope shaft. Alternatively or additionally, it is also possible to realize a lateral viewing direction by prisms or mirrors arranged distally to the objectives.

The projection objectives can also be rod lenses or rod lens systems, as result of which the design of the optical unit can be simplified.

A projection objective can be arranged or displaced laterally to an optical axis of another projection objective or of a plurality of other projection objectives, and laterally to the optical axis of the collimating optical unit, as a result of which it is possible to enable good matching between the dimensions of the image sensor and the dimensions of the endoscope. Alternatively or additionally, the optical components, the collimating optical units and/or the image sensors can have a lateral offset from one another, as a result of which it is possible to generate a change in the lateral offset between the two stereoscopic partial images. Vignetting of the image can be avoided in the case of such displacement of the projection objective if the following condition is satisfied:

$$s \leq \frac{D_p - D_k}{2}$$

where s is the path of the lateral displacement, $D_p$ is the diameter of the free opening of the projection objective and $D_k$ is the diameter of the emerging parallel beam path at the location of the projection objective.

BRIEF DESCRIPTION OF THE DRAWINGS

The invention is now intended to be explained in more detail on the basis of exemplary embodiments depicted schematically in the figures. In detail.

DETAILED DESCRIPTION

Figure 1:
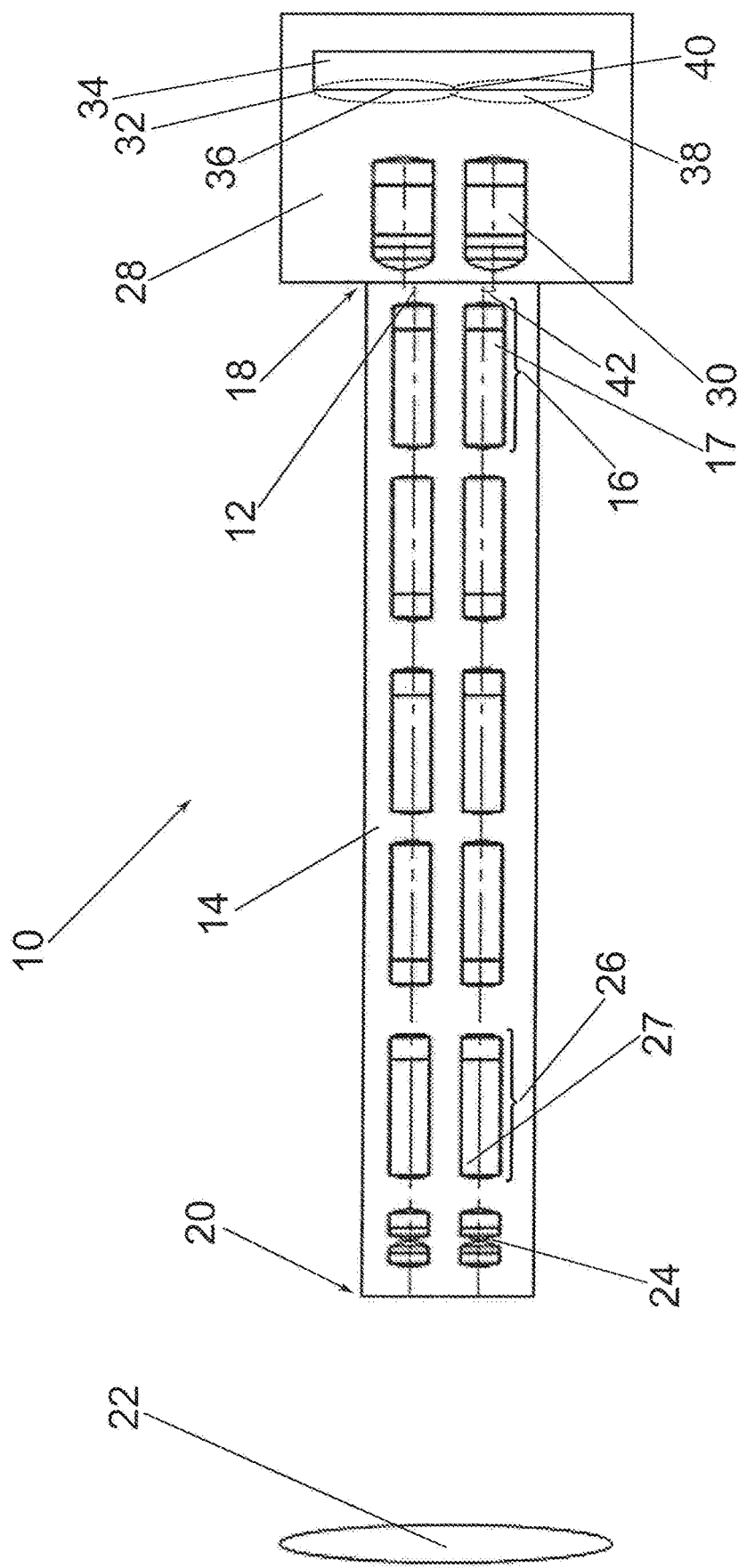
FIG. 1 shows a schematic illustration of a first exemplary embodiment of a video endoscopic device with a lateral distance between the stereoscopic partial images which has been increased by a projection objective arranged off centre.

FIG. 1 shows a schematic illustration of a first exemplary embodiment of a video endoscopic device 10 with two parallel beam paths 12 which extend through the interior of an endoscope shaft 14 and are collimated by a respective collimating rod lens system 16 at the proximal end 18 of the endoscope shaft 14.

An object 22 situated in front of the distal end 20 of the endoscope shaft 14 is imaged by means of two parallel objectives 24. The image generated near the distal end 20 of the endoscope shaft 14 by the objectives 24 is transmitted, by means of two image guiding rod lens system arrangements which are arranged in parallel and made of a plurality of rod lens systems 26 arranged coaxially with one another, in the direction of the proximal end 18 of the endoscope shaft 14 and is collimated there by the collimating rod lens systems 16. The rod lens systems 16, 26 can consist of cemented rod lenses 17, 27 and/or of other lenses cemented therewith.

The proximal end 18 of the endoscope shaft 14 is connected to a camera head 28, in which the beam paths 12 extending parallel from the collimating rod lens systems 16 are projected by a respective projection objective 30 onto a recording plane 32 of a sensor 34. By focusing on a focus 36 in the recording plane 32 of the image sensor 34, it is possible to generate a respective stereoscopic partial image 38 which has an overlap 40. Perpendicular to a third optical axis of the collimating rod lens systems 16, which generate the respective parallel beam path 12, the respective projection objective 30 is offset by a small lateral offset 42 such that a second optical axis of the respective projection objective 30 is offset by a small lateral offset 42, i.e. the lateral distance between the projection objectives 30 is greater than the lateral distance between the collimating rod lens systems 16, as a result of which the distance between the two stereoscopic partial images 38 can be increased. The respective projection objective 30 is preferably arranged such that the second optical axis is arranged laterally offset to the respective rod lens system 16 by at most half a diameter of the projection objective 30 to the third optical axis of said respective rod lens system 16. The respective projection objective 30 can also be arranged coaxially with the respective rod lens system 16.

The respective collimating rod lens system 16 can also be arranged such that the third optical axis is laterally offset from a common first optical axis of the respective image guiding rod lens system 26; here, the collimating rod lens system 16 is preferably arranged such that the third optical axis is offset (not shown here) by at most half a diameter of the collimating rod lens system 16 from the common first optical axis of the image guiding rod lens system 26. In place of a rod lens system 16, the optical unit used for collimating the beam path 12 can also be a rod lens 17. Preferably, the rod lens systems 16 used for the collimation are of the same design as the rod lens systems 26 used for image guidance or image transmission. The rod lenses 17, 27 used in the rod lens systems 16, 26 can have dimensions which are identical to one another or differ from one another.

In an exemplary embodiment (not shown here), prisms at the distal end 20 of the endoscope shaft 14 can be arranged distally from the other optical components. Moreover, the prisms can be cemented to the other optical components.

Figure 2:
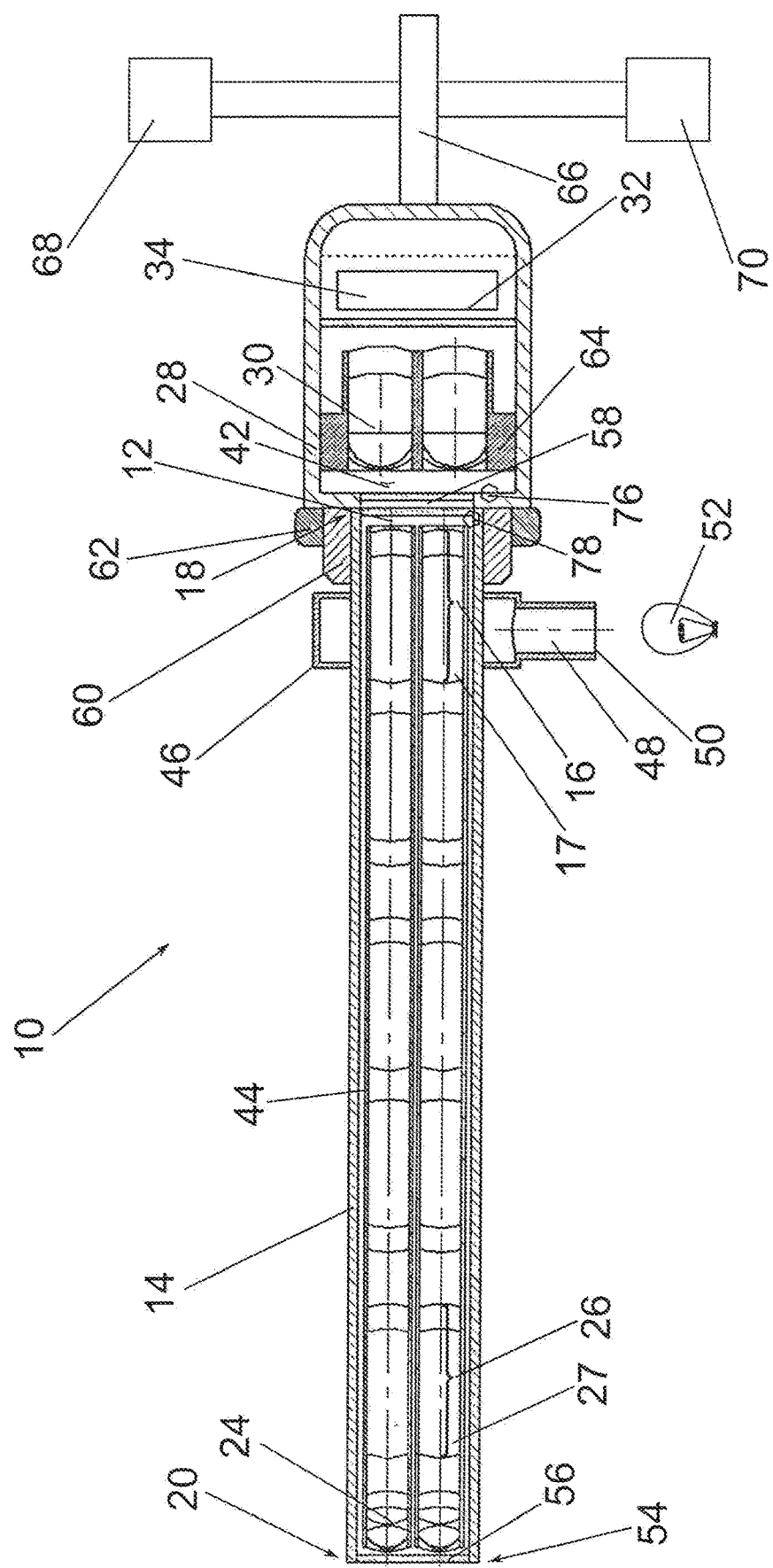
FIG. 2 shows, in the longitudinal section, a schematic illustration of a second exemplary embodiment of a video endoscopic device with a lateral distance between the stereoscopic partial images which has been increased by a projection objective arranged off centre.

FIG. 2 shows, in the longitudinal section, a schematic illustration of a second exemplary embodiment of a video endoscopic device 10 with a similar design as the first exemplary embodiment. The respective optical components of the parallel optical arrangements, i.e. the objectives 24, the image guiding rod lens systems 26 and the collimating rod lens systems 16, are enclosed by two tubes 44 arranged in parallel, which are arranged in the endoscope shaft 14.

Additionally, an illumination device 46 is connected to the endoscope shaft 14, which illumination device contains an optical waveguide 48 which, via an illumination-light inlet 50, transmits light from a light source 52 in the distal direction along the endoscope shaft 14, which light illuminates the object plane 22 by an illumination-light outlet 54. The optical waveguide 48 can be connected to the endoscope shaft 14 in either a releasable and re-lockable or rigid manner. The illumination-light inlet 50 can also be connected to a light source 52 by means of a flexible optical fibre cable (not shown here). Moreover, the light source 52 and the illumination-light inlet 50 of an optical waveguide 48 can also be arranged in the camera head 28 (not shown here).

From the object plane 22, an image is transmitted to the objectives 24 through a transparent protective window 56 arranged at the distal end 20 of the endoscope shaft 14, from which objectives the image is guided, as described for the first exemplary embodiment, through the tubes 44 arranged in parallel from the distal end 20 to the proximal end 18 of the endoscope shaft 14. At the proximal end 18 of the endoscope shaft 14, the image, in a parallel beam path 12, reaches the camera head 28 through a light inlet 56, wherein further transparent protective windows 56 are arranged at the proximal end 18 of the endoscope shaft 14 and on the light inlet 58 of the camera head 28. In the camera head, the parallel beam path 12 is projected by the projection objective 30 through a further transparent protective window 56 onto the recording plane 32 of the image sensor 34, wherein a larger lateral offset 42 leads to an increased distance between the stereoscopic partial images 38 on the recording plane 32 of the image sensor 34.

In this exemplary embodiment, the camera head 28 is connected to the endoscope shaft 14 by means of a releasable and re-lockable coupling 60. By means of an operating element 62 arranged in the direction of the endoscope shaft, a focusing device 64 connected to the projection objectives 30 can focus the stereoscopic partial images 38 onto the recording plane 32 of the image sensor 34. To this end, the operating element 62 can e.g. be rotated, as a result of which the focusing device 64 can be displaced axially, i.e. along the axis of the beam path 12, in this case along the respective second optical axis of the respective projection objective 30. The focusing device 64 can also be configured in such a way that the individual projection objectives 30 can be displaced axially (not shown here). Alternatively or additionally, other optical components can also be displaced axially with respect to one another (not shown here).

Arranged proximally behind the camera head 28 is a cable 66, which can be used for power supply and data transfer. An image processor 68 and a memory unit 70 are connected to the cable 66 in this exemplary embodiment.

The image processor 68 can convert the two stereoscopic partial images 38 projected onto the image sensor 34 into an image signal which can be depicted on stereoscopic screens, for example according to the polarization principle, shutter-glasses principle or the like. One of the objects of the image processor 68 can be to improve the image signal by means of image processing; in particular, an image improvement can be achieved by image-improving measures such as, for example, adaptation of contrast, colour display, improvements in the focus, correction of distortion, image-position deviations, instances of masking, adaptation of the stereoscopic vergence and/or compensation of tolerances in the image scale. Moreover, the image processor 68 can also be arranged within the video endoscopic device 10 (not shown here), for example in the camera head 28 or in the endoscope shaft 14.

The memory unit 70 can save calibration data for calibrating the video endoscopic device 10. When interchanging components, such as for example the endoscope shaft 14 and/or the camera head 28, a recalibration can be performed and the calibration data for the new component arrangement can be saved. Alternatively or additionally, calibration data can be loaded for parts of or the whole component arrangement from the memory unit 70 in order to re-establish the readiness for use of the video endoscopic device 10. The memory unit 70 can also be arranged in the camera head 28 or in the endoscope shaft 14 (not shown here).

In this exemplary embodiment, the camera head 28 additionally contains a sensor device 76, for example an RFID transceiver or the like, and the endoscope shaft 14 contains a marking 78, for example an RFID transponder or the like, situated in the vicinity of, or on, the proximal end 18 of the endoscope shaft 14, readable by the sensor device 76. When the camera head 28 is connected to a new endoscope shaft 14, the sensor device 76 can identify the readable marking 78 on the endoscope shaft 14 and transmit a signal to the memory unit 70 via the cable 66. Stored sets of predetermined calibration data for the various arrangements of the optical components can be saved in the memory unit 70, which calibration data emerge from the connection of endoscope shaft 14 and camera head 28. Due to the signal from the sensor device 76, the memory unit 70 can select the calibration data or the calibration data with the best fit for the newly connected components and use these data to calibrate the video endoscopic device 10.

Figure 3:
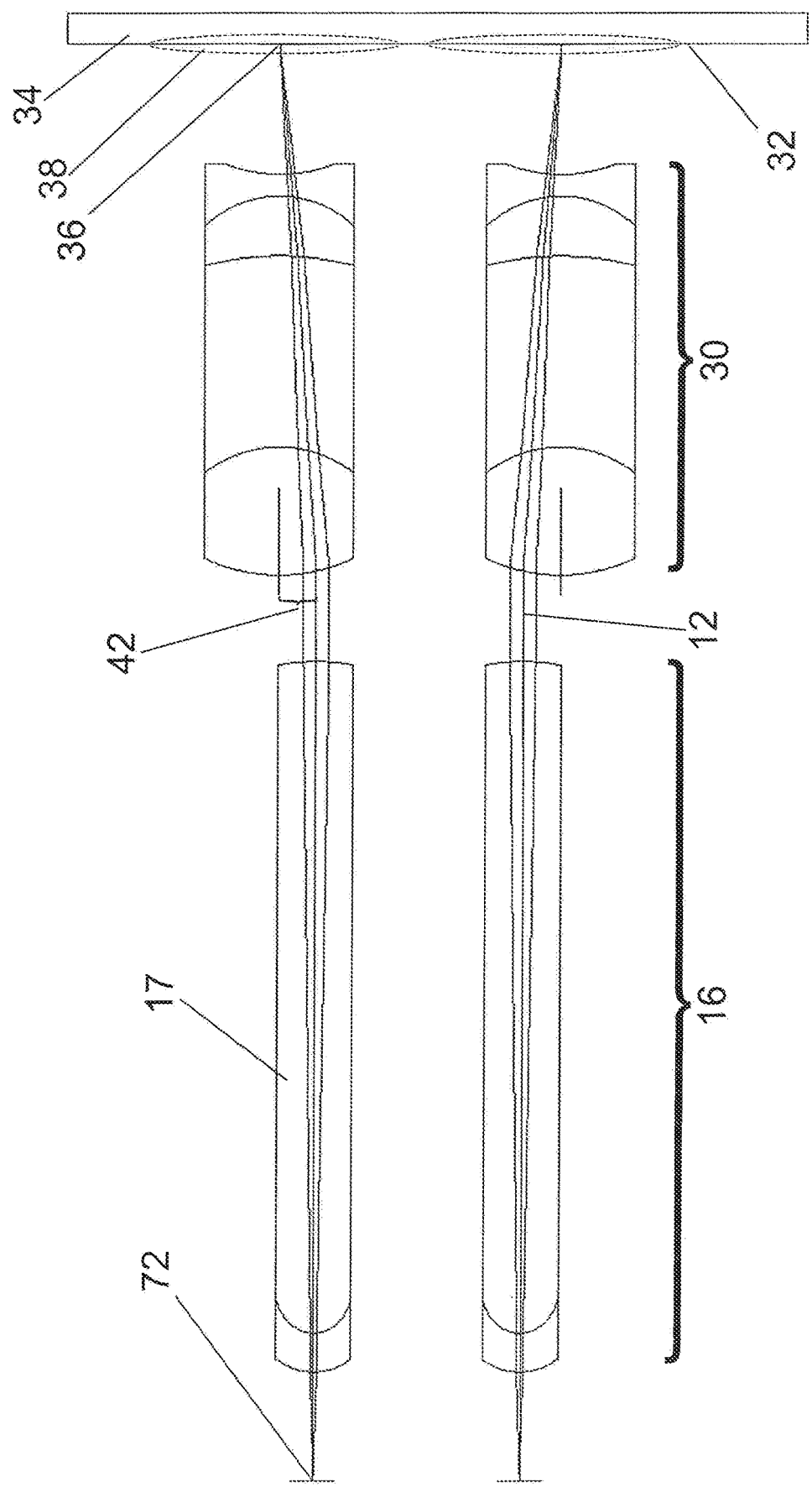
FIG. 3 shows a respectively exemplary beam path of exemplary collimating rod lens systems with projection objectives not arranged coaxially therewith.

FIG. 3 shows two exemplary parallel beam paths 12 through two exemplary, collimating rod lens systems 16 with projection objectives 30 not arranged coaxially therewith. An image point at the respective focus 72 of the respective collimating rod lens system 16 is imaged on an imaging focus 36 situated in the recording plane 32 of the image sensor 34 by means of the collimating rod lens systems 16 and the projection objectives 30 arranged proximally therefrom. The lateral distance between the stereoscopic partial images 38 has increased as a result of the lateral offset 42 which emerges from the larger lateral distance between the projection objectives 30 compared to the collimating rod lens systems 16; this, in particular, becomes clear on the basis of an image point in the focus 36 in the recording plane 32 of the image sensor 34.

The incident parallel beam paths 12 enter into a respective projection objective 30 with the lateral distance 42 and emerge at different angles from the respective projection objective 30. The lateral distance 42 between the third optical axis of the respective collimating rod lens system 16 and the second optical axis of a respective projection objective 30 therefore generates a directional deflection of the respective collimated parallel beam paths 12, as a result of which these are projected onto one or more foci 36 in the recording plane 32 of the image sensor 34 as two coaxially offset stereoscopic partial images 38 by the respective projection objective 30.

In one exemplary embodiment (not shown here), one or more image field stops can be arranged in, or in the vicinity of, one of the intermediate image planes of the video endoscopic device 10. These image field stops can have such a form that a visual field is imaged as an in-focus dark edge into the recording plane 32 and/or it is rendered possible, or made easier, to identify size and location of an image field and/or identify an employed endoscope shaft 14 or endoscope type by means of imaging electronics, for example the image sensor 34. In a further exemplary embodiment (not shown here), such an image field stop is arranged in each case in the image field plane situated closest to the collimating optical units 16. Furthermore, respectively one such image field stop can be arranged in the image field plane situated closest to the objectives 24 arranged at the distal end 20 the endoscope shaft 14 (not shown here).

In one exemplary embodiment (not shown here), a displaceable visual field stop can be arranged in one of the parallel beam paths 12, as a result of which the parallel beam path 12 can be blocked and/or delimited temporarily or permanently. The visual field stop can be displaced between the two parallel beam paths 12 and thus in each case block or delimit one of the stereoscopic partial images 38. It is also possible for a plurality of different visual field stops to be arranged in the video endoscopic device 10 (not shown here).

In a further exemplary embodiment (not shown here), it is also possible for prisms and/or mirror arrangements to be arranged behind and/or in a respective projection objective 30 (not shown here).

Figure 4:
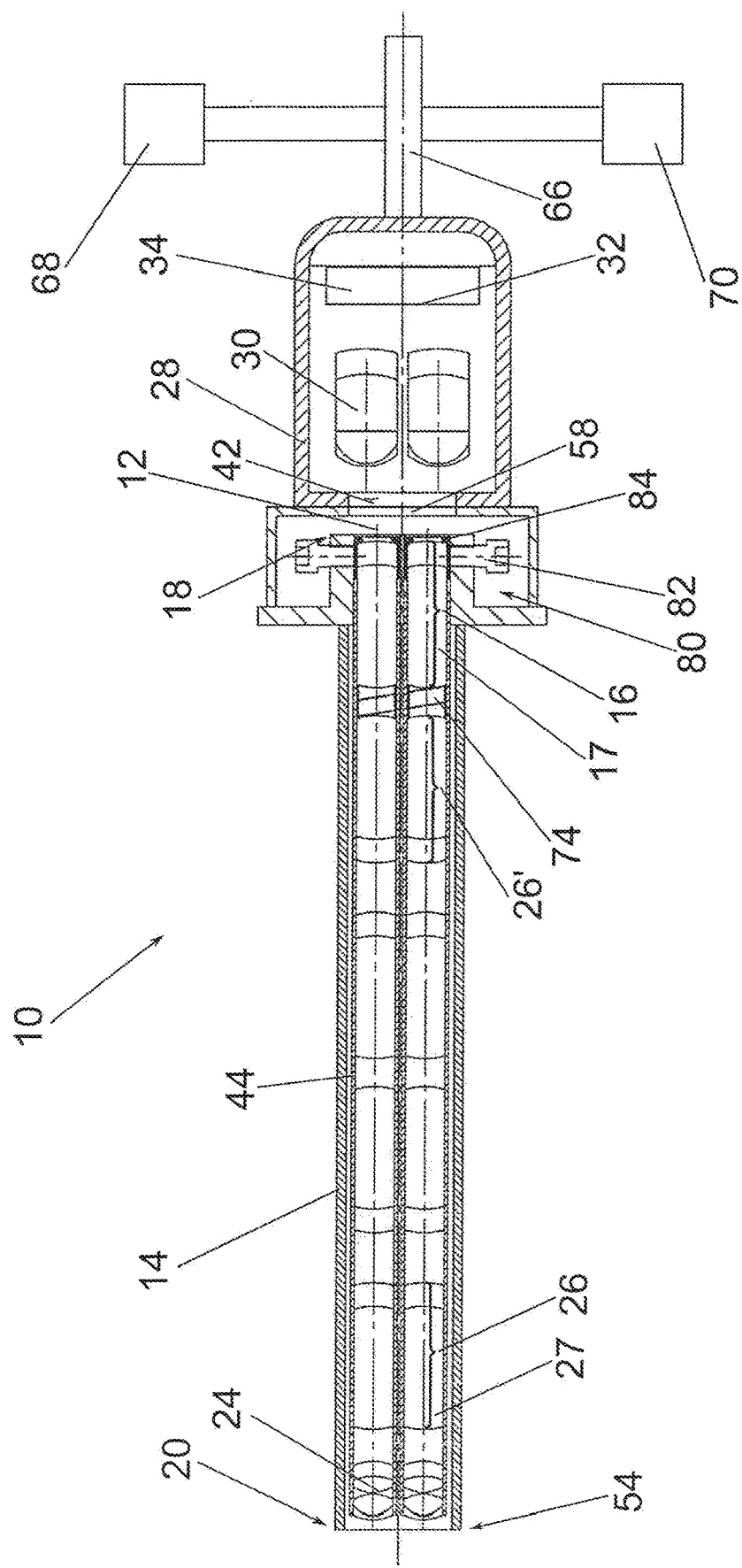
FIG. 4 shows a schematic illustration of a third exemplary embodiment of a video endoscopic device with a mechanical spring for setting an axial distance between adjacent optical components.
Figure 5:
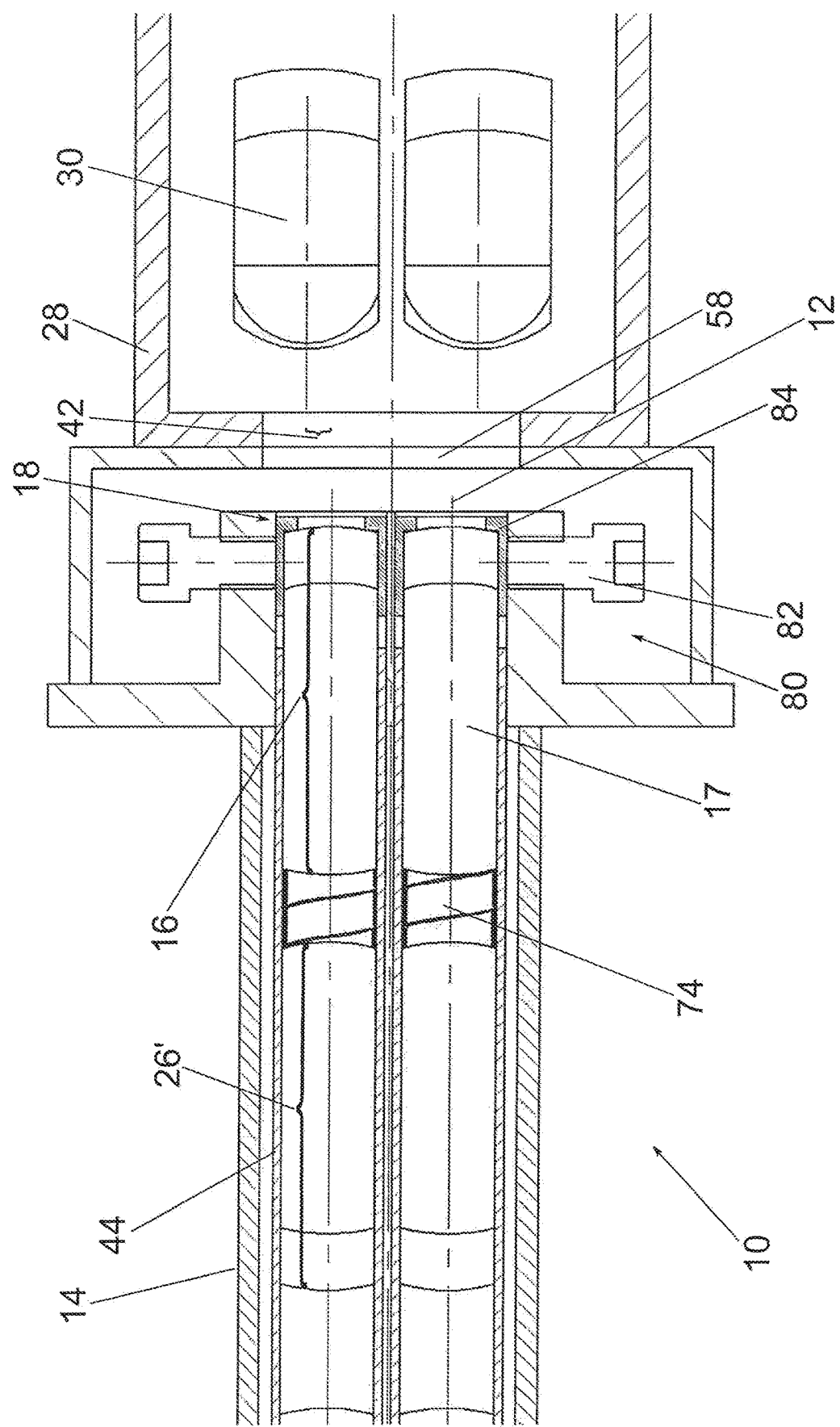
FIG. 5 shows a schematic illustration of a section of the third exemplary embodiment of the video endoscopic device with a protective cap at the proximal end of the video endoscopic device.

FIG. 4 shows a schematic illustration of a third exemplary embodiment of a video endoscopic device 10 with a mechanical spring 74 for setting an axial distance between the successive optical components 26' and 16. Instead of the mechanical spring 74, use can also be made of e.g. a gas spring or a different resilience element. A combination of the mechanical spring 74 with a different resilience element, for example a gas mixture, a gas, a liquid or a solid, is also conceivable. In the shown exemplary embodiment, the mechanical spring 74 is arranged in an air atmosphere, i.e. in a gas mixture. The mechanical spring 74 serves to set an axial distance between the two successive optical components 26' and 16 such that mechanical play between the components is prevented. Here, mechanical play is prevented, or at least reduced, by the spring effect of the mechanical spring 74. It is also possible for a plurality of mechanical springs 74 or combinations of resilience elements to be arranged between a plurality of successive optical components along the endoscope shaft 14 (not shown here), for example between all optical components of a respective parallel arrangement. FIG. 5 shows a magnified section of the third exemplary embodiment of the video endoscopic device 10 with a mechanical spring 74.

The design of the third exemplary embodiment of the video endoscopic device 10 is similar to the design of the second exemplary embodiment of the video endoscopic device 10 shown in FIG. 2. The design substantially differs by the mechanical spring 74 and by a clamping device 80 which is arranged proximally toward the proximal end 18 of the endoscope shaft 14. The clamping device 80 surrounds the collimating rod lens systems 16, partially arranged in the tubes 44, and part of the tubes 44. The clamping device 80 connects the endoscope shaft 14 with the camera head 28 and contains set screws 82 in order to set a pressure force on a termination cap 84 which surrounds part of the respective collimating rod lens system 16. The set screws 82 are continuously adjustable in order to set a pressure force on the termination cap 84, which renders it possible to restrict the freedom of movement of the collimating rod lens system 16, particularly in the direction of the spring effect. By means of this, a holding state or locked state of the clamping device 80 can be set by means of the set screw 82, which state is reached when the pressure force on the termination cap 84 is sufficient to prevent an axial and lateral movement of the collimating rod lens systems 16. In the locked state, the proximal ends of the collimating rod lens systems 16 or the proximal ends of the termination caps 84 are held at a fixed axial distance to the tubes 44 surrounding the optical components. In a loosened or open state of the clamping device 80, it is possible to set the axial distance between the proximal ends of the collimating rod lens systems 16, or the proximal ends of the termination caps 84, and the tubes 44, in which the optical components are arranged.

Figure 6:
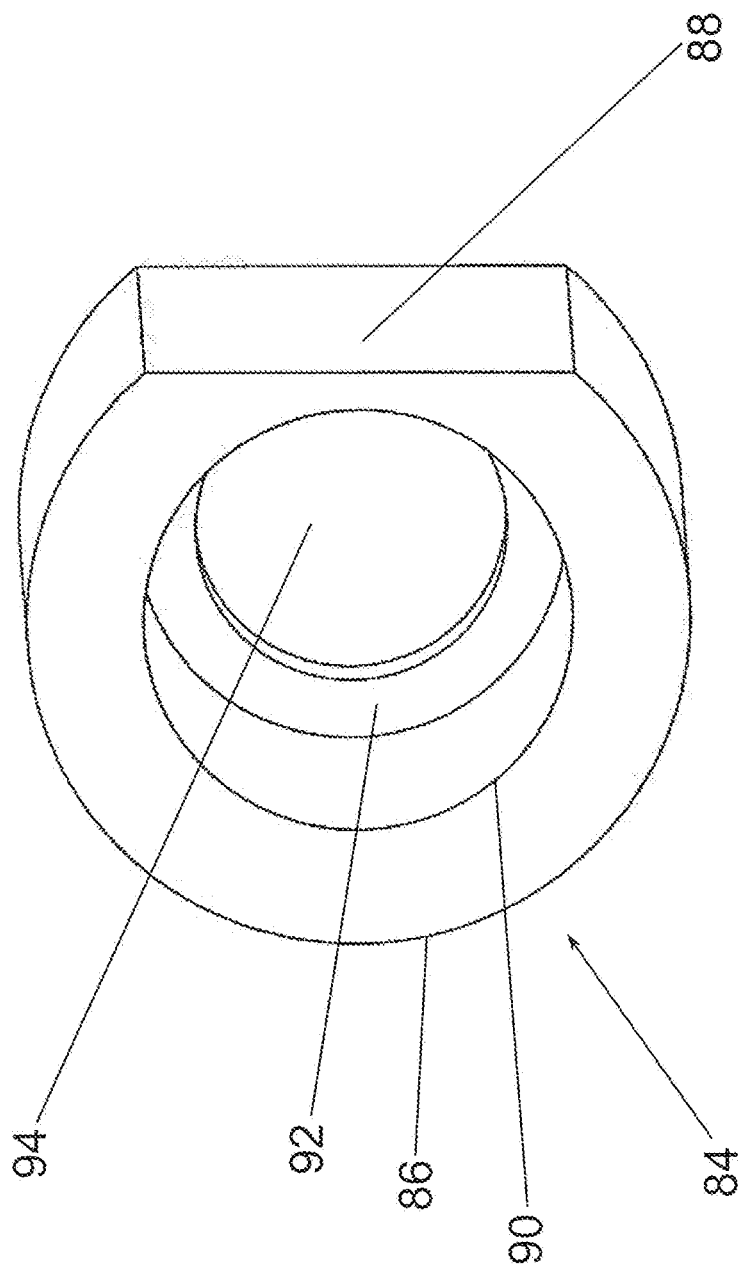
FIG. 6 shows a schematic illustration of a cylindrical termination cap with a flattening on one side.

FIG. 6 shows an exemplary embodiment of a termination cap 84. The termination cap 84 has a cylindrical outer surface 86 with a one-sided flattening 88 along a longitudinal axis of the termination cap 84 and thus forms a hollow cylinder-shaped tube with an internal diameter 90. As a result of the hollow cylinder shape, the termination cap 84 can surround a collimating rod lens system 16 (see FIG. 5). Moreover, the termination cap 84 has a projection 92, which, in a circular shape, surrounds an opening 94 along a proximal end of the termination cap 84 and is provided to delimit the freedom of movement of the surrounded collimating rod lens system 16. Alternatively or additionally, the respective collimating rod lens system 16 can also be permanently fastened, for example adhesively bonded, to the termination cap 84 and/or the proximal end of the termination cap 84. The opening 94 allows the parallel beam path 12 generated by the collimating rod lens system 16 to pass the termination cap 84.

In an alternative exemplary embodiment (not shown here), an optical window transparent to visible radiation or light is arranged in the opening 94. The termination cap 84 can be hermetically sealed with the aid of a seal, as a result of which the tubes 44, in which the collimating rod lens systems 16 are situated, are also hermetically sealed. To this end, in particular, the proximal end of the termination cap 84 with the window is hermetically sealed. By way of example, a hermetic seal can alternatively also be achieved by virtue of the termination cap 84 with the opening 94 without a window being surrounded by a hermetically sealed protective cap with a window (not shown here). In one exemplary embodiment (not shown here), the protective cap is configured to be screwed onto the termination cap 84 or the termination caps 84, which surround the proximal end of the collimating rod lens systems 16.

Figure 7:
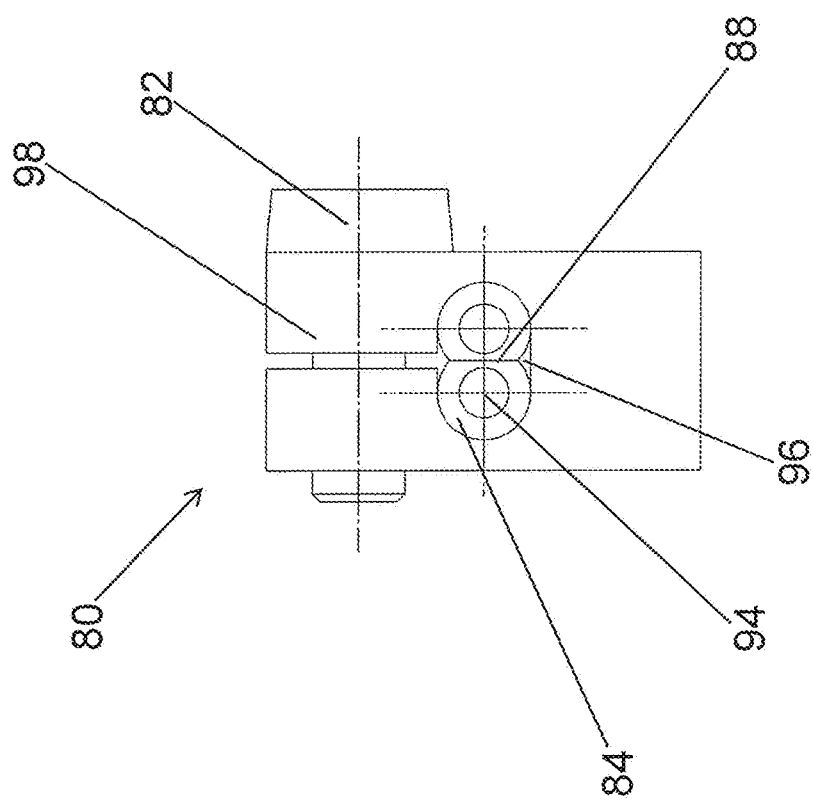
FIG. 7 shows a schematic illustration of an exemplary embodiment of a clamping device with cylindrical termination caps.

FIG. 7 shows a further exemplary embodiment of the clamping device 80. The clamping device 80 has a slotted block 98 with a set screw 82 and a slot 96 for holding the termination caps 84. The termination caps 84 are arranged in the slot 96 and contact one another at the flattenings 88 thereof. In the case of sufficient distance between the parallel arrangements of the optical components, the video endoscopic device 10 can also comprise two separate parallel arrangements of the optical components in two round holes with the slot and separate clamping devices 80 (not shown here). In this case, the termination caps 84 do not have a flattening 88 (not shown here).

The clamping device 80 can form part of the endoscope shaft 14 or part of the camera head 28 or can be an independent component of the video endoscopic device 10. The clamping device 80 can comprise (not shown here) one or more sensor devices, for example an RFID transceiver or the like, and/or a marking, for example an RFID transponder or the like, which can be read by another sensor device. The sensor devices and readable markings can be arranged in such a way that when the clamping device 80 is connected to an endoscope shaft 14 and/or to a camera head 28, the respective sensor devices of the components of the video endoscopic device 10 identify the readable marking on the respective other component such that, when the components are brought together, there is automatic identification of the components of the video endoscopic device 10.

Figure 8:
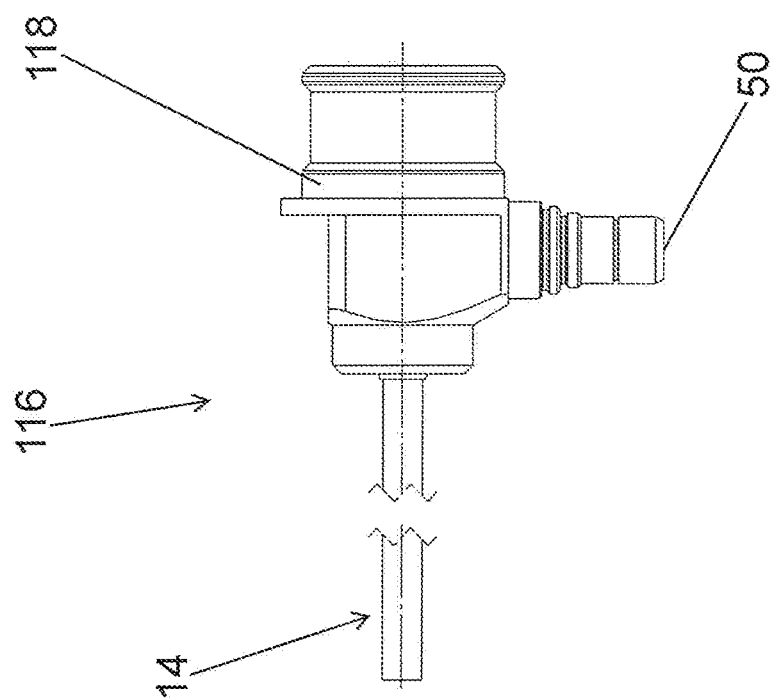
FIG. 8 shows a schematic illustration of an exemplary embodiment of an endoscope in a side view.

FIG. 8 shows an exemplary embodiment of an endoscope 116 in a side view. The proximal end of the endoscope 116 has a coupling half 118, which is provided for connecting the endoscope 116 to the camera head 28, or for locking it on the latter, by means of a second coupling half 118' of the camera head 28 (see FIG. 10). The light inlet 50 is configured in such a way that flexible optical waveguides can be connected thereto. For clarity, the endoscope shaft 14 is depicted in a shortened form.

Figure 9:
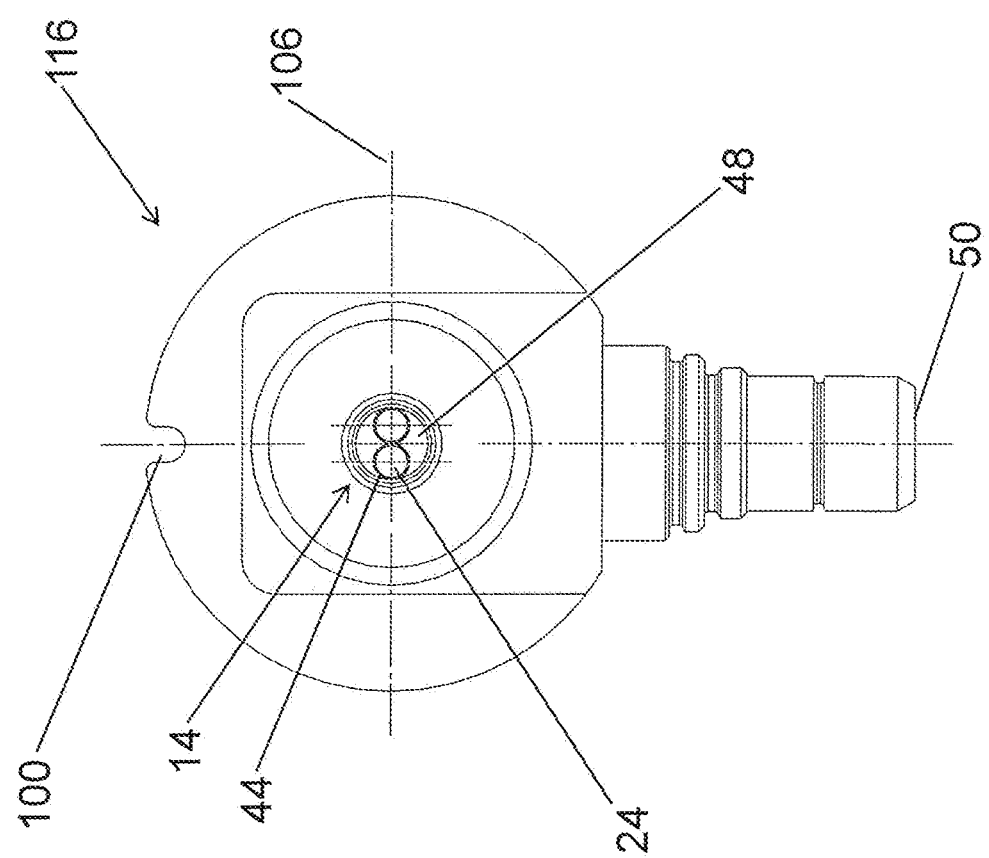
FIG. 9 shows a schematic illustration of a distal end of the exemplary embodiment of the endoscope.

FIG. 9 shows a schematic illustration with a view of the distal end of the exemplary embodiment of the endoscope 116 from FIG. 8. The two objectives 24 arranged in the endoscope shaft 14 are surrounded by the tubes 44. The free cross section within the opening of the endoscope shaft 14 is filled with bundles of optical waveguides 48. The objectives 24 are arranged in such a way that a stereoscopic horizon 106 of the endoscope 116, which is formed by a line connecting the two objectives 24, is arranged horizontally. An anti-rotation device 100, which is a slot in the depicted exemplary embodiment of FIG. 9, is situated in the vicinity of the proximal end of the endoscope 116. The anti-rotation device 100 interacts with a second anti-rotation device 100', which is situated on the camera head 28 and is a pin in the exemplary embodiment shown in FIG. 10. The anti-rotation devices 100 and 100' can have anti-rotation device elements which can be inserted into one another in an interlocking manner, for example boreholes, slots, bolts, pins or the like, and combinations thereof. The anti-rotation device 100 is situated at a fixed location with respect to the stereoscopic horizon 106 of the endoscope 116 and prevents changes in the alignment of the stereoscopic partial images when locking the endoscope 116 on the camera head 28 (FIG. 10).

Figure 10:
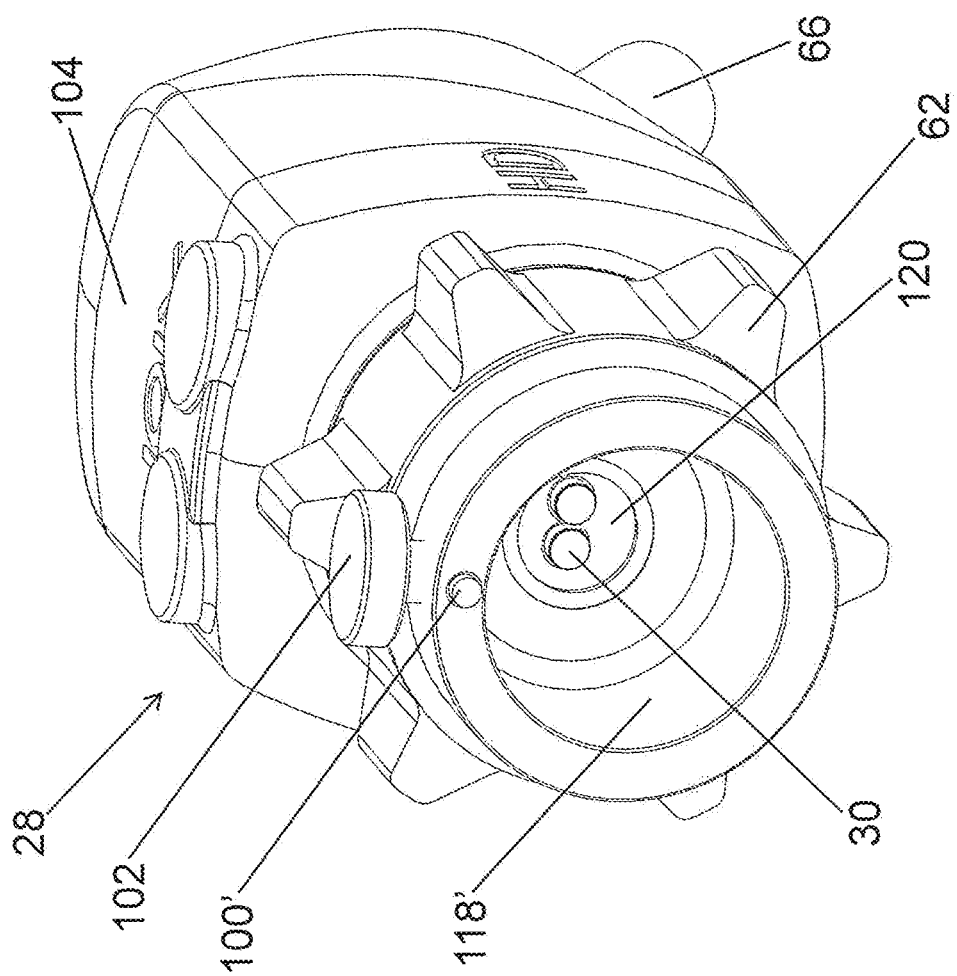
FIG. 10 shows a schematic illustration of an exemplary embodiment of a camera head.

FIG. 10 shows an exemplary embodiment of a camera head 28. The camera head 28 has a coupling half 118' which comprises an anti-rotation device 100' in the form of a pin and a screw 102. The coupling half 118' is arranged distally from an operating element 62 which surrounds an objective carrier 120 with projection objectives 30. A camera housing 104, which is connected to a stereoscopic screen (not shown here) via a cable 66, is situated proximally from the projection objectives 30. Alternatively or additionally, the camera head 28 can also be connected to e.g. a computer or another evaluation unit.

The coupling half 118' serves for connecting an endoscope 116. To this end, the coupling half 118' is connected to the coupling half 118 of the endoscope 116. The screw 102 serves as a releasable locking element for locking the coupling half 118 of the endoscope 116. The anti-rotation device 100' in the form of a pin serves to prevent changes in the alignment of the stereoscopic partial images. In the case of a rotation of the operating element 62, there is a common axial translation of the projection objectives 30 arranged in the objective carrier 120. As a result of this, a user can focus the video endoscopic device 10 manually by the operating element 62.

Figure 11:
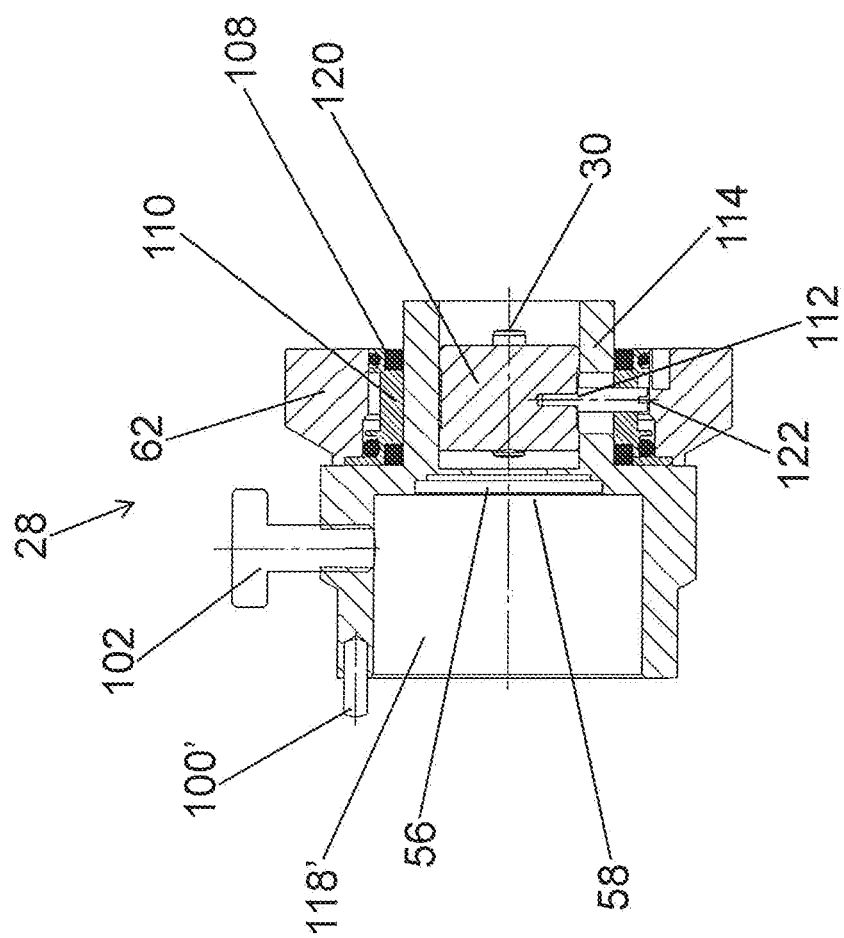
FIG. 11 shows a schematic sectional view of part of the exemplary embodiment of the camera head.

FIG. 11 shows a section through part of the exemplary embodiment of the camera head 28 shown in FIG. 10. The camera head 28 has a coupling half 118' with an anti-rotation device 100' for connecting the camera head 28 to an endoscope 116. It is possible to connect various endoscopes 116 to the camera head 28, which endoscopes can be selected in accordance with a specific application, in particular a medical application. The anti-rotation device 100' interacts with a second anti-rotation device 100 on the endoscope 116, and so a rotation of the endoscope 116 with respect to the camera head 28 is prevented. A screw 102 serves to lock a corresponding coupling half 118 of the endoscope 116 (see FIG. 8).

A light inlet 58 of the camera head 28 with a transparent protective window 56 is arranged proximally from the coupling half 118', which light inlet is surrounded by a camera tube 114. Light from an endoscope 116 connected to the camera head 28 (not shown here) is incident through the light inlet 58 on an objective carrier 120, which carries the projection objectives 30.

The objective carrier 120 is securely connected to a pickup 112, which projects through the camera tube 114 and into a helix-shaped slot 122 of a focusing ring 110. The pickup 112 is functionally connected to the operating element 62 by means of the helix-shaped slot 122 of the focusing ring 110. The focusing ring 110 is mounted rotatably in the camera tube 114 and securely connected to the operating element 62 such that the focusing ring 110 is rotated when the operating element 62 is rotated. By means of the helix-shaped slot 122, the pickup 112 is driven when the focusing ring 110 is rotated, and so the objective carrier 120 is not co-rotated when the focusing ring 110 is rotated.

The camera head 28 has a sealing element 108, which is arranged between operating element 62 and camera tube 114 and serves to hermetically seal the camera head 28.

The camera head 28 has further components or component parts (not depicted here), which are arranged in or on the camera head 28. By way of example, these include the camera housing 104, a plurality of protective windows, the image sensor or sensors and further components or component parts with mechanical and electronic functions.

LIST OF REFERENCE SIGNS

10 Video endoscopic device
12 Parallel beam path
14 Endoscope shaft
16 Collimating rod lens system
17 Collimating rod lens
18 Proximal end of the endoscope shaft
20 Distal end of the endoscope shaft
22 Object
24 Objective
26 Image guiding rod lens system
26 Image guiding rod lens
28 Camera head
30 Projection objective
32 Recording plane
34 Image sensor
36 Focus
38 Stereoscopic partial image
40 Overlap of the stereoscopic partial images
42 Lateral offset
44 Tube
46 Illumination device
48 Optical waveguide
50 Illumination-light inlet
52 Light source
54 Illumination-light outlet
56 Transparent protective window
58 Light inlet of the camera head
60 Releasable and re-lockable coupling
62 Operating element
64 Focusing device
66 Cable
68 Image processor
70 Memory unit
72 Focus of the rod lens system
74 Mechanical spring
76 Sensor device
78 Readable marking
80 Clamping device
82 Set screw
84 Termination cap
86 Cylindrical outer surface
88 One-sided flattening
90 Internal diameter
92 Projection
94 Opening
96 Slot
98 Slotted block
100 Anti-rotation device
102 Detachable locking element
104 Camera housing
106 Stereoscopic horizon
108 sealing element
110 Focusing ring
112 Pickup
114 Camera tube
116 Endoscope
118 Coupling half
120 Objective carrier
122 Helix-shaped slot

What is claimed is:

1. A video endoscopic device comprising
a set of different interchangeable endoscopes with different stereoscopic base lengths, each of the interchangeable endoscopes comprising two parallel optical arrangements, which, together, are arranged at least in part in the interior of a respective one of the interchangeable endoscopes shaft of an endoscope and each comprise optical components, arranged coaxially with one another along a common first optical axis of the optical components of a respective optical arrangement, each optical arrangement being configured to transmit an optical image from a distal end of the respective optical arrangement to a proximal end of the respective optical arrangement,
said video endoscopic device further comprising a camera head, releasably connected to the endoscope shaft by a mechanical coupling, the camera head arranged adjacent to or adjoining the proximal ends of the optical arrangements, whereby the camera head can be connected to different interchangeable endoscopes of the set of different interchangeable endoscopes, the camera head comprising:
at least one image sensor having at least one recording plane, said camera head further comprising at least two projection objectives, of which each one has a second optical axis and is arranged and configured to project an image onto the image sensor,
wherein the optical arrangements each comprise a collimating optical unit, arranged at the respective proximal end of the optical arrangement and thus at a proximal end of the endoscope shaft thereof, for generating an at least approximately parallel beam path at the outlet of the respective optical arrangement,
wherein the respective collimating optical unit has a third optical axis that is arranged coaxially with the optical components of the optical arrangements or laterally offset by at most half a diameter of the collimating optical unit from the common first optical axis of the optical components of the optical arrangements, and each one of the at least two projection objectives is arranged and configured to image the parallel beam path, generated by a respective collimating optical unit, on at least one focus in the at least one recording plane of the at least one image sensor and
wherein at least one of the projection objectives is arranged so that the respective second optical axis has a lateral distance, measuring at most half a diameter of the projection objective, from the third optical axis of the collimating optical unit which generates the parallel beam path, the at least one projection objective being arranged and configured for imaging said parallel beam path on the at least one focus, and wherein no deflecting optical element is arranged between the collimating optical unit and the respective projection objective as a result of which the parallel beam path enters the at least one projection objective off-center with a lateral distance from the second optical axis of the at least one projection objective,
wherein the lateral distance between the projection objectives of the camera head is larger than the lateral distance between the collimating optical units of the endoscope shaft, and further wherein each of the set of different interchangeable endoscopes can be connected with the camera head without a need for adapting the arrangement of the at least one of the projection objectives in order to adapt the lateral distance between the second optical axis and the third optical axis.

2. The video endoscopic device according to claim 1, wherein the optical components, respectively arranged coaxially with one another, comprise rod lenses.

3. The video endoscopic device according to claim 1, wherein the collimating optical units for generating an at least approximately parallel beam path comprise rod lenses at the outlet of the optical arrangements.

4. The video endoscopic device according to claim 1, wherein the collimating optical units for generating an at least approximately parallel beam path at the outlet of the optical arrangements are rod lens systems comprising at least two cemented lenses, wherein at least one of the lenses of the rod lens system comprising two cemented lenses is a rod lens.

5. The video endoscopic device according to claim 1, wherein the video endoscopic device comprises rod lens systems for the purposes of collimation, which are of the same design as the rod lens systems employed for image transmission.

6. The video endoscopic device according to claim 1, wherein each one of the at least two projection objectives is arranged such that the second optical axis is arranged offset laterally by at most half a diameter of the projection objective to the optical axis of the optical components of the respective optical arrangement.

7. The video endoscopic device according to claim 1, wherein at least one of the parallel optical arrangements comprises a resilience element arranged between two successive optical components and wherein the resilience element is configured to ensure an axial distance between the two successive optical components such that mechanical play between the optical components is reduced.

8. The video endoscopic device according to claim 7, wherein the resilience element is arranged between an optical component, arranged closest to the collimating optical unit, of the at least one of the parallel optical arrangements and the collimating optical unit.

9. The video endoscopic device according to claim 7, wherein the video endoscopic device comprises a holding device at the proximal end of the parallel optical arrangements and wherein the holding device is configured to hold the collimating optical units of the parallel optical arrangements in such a way that, in a locked state of the holding device, an axial and/or lateral movement of the collimating optical units is prevented.

10. The video endoscopic device according to claim 9, wherein the endoscope shaft comprises an illumination device for illuminating an object plane and wherein the illumination device comprises optical waveguides, which transmit the light from at least one light source from an illumination-light inlet arranged in the vicinity of, or at, the proximal end of the endoscope shaft to an illumination-light outlet arranged in the vicinity of, or at, the distal end of the endoscope shaft, wherein the at least one light source is contained in the camera head and/or connected to the endoscope shaft in either a releasable and re-lockable or rigid manner by a flexible optical waveguide.

11. The video endoscopic device according to claim 1, wherein an image processor is arranged within or outside of the video endoscopic device and configured to convert two stereoscopic partial images projected onto the at least one image sensor into an image signal which can be depicted on stereoscopic screens.

12. The video endoscopic device according to claim 11, wherein the image processor is configured to perform image-improving measures by means of image processing.

13. The video endoscopic device according to claim 1, wherein the video endoscopic device comprises at least one interchangeable component.

14. The video endoscopic device according to claim 13, wherein, when interchanging at least one component, the newly connected components can be calibrated with respect to one another by a set of predetermined calibration data stored in a memory unit and wherein the video endoscopic device comprises at least one sensor device which can read and process at least one readable marking on at least one of the components in order to select, from a number of items of predetermined calibration data in the memory unit, the calibration data or the calibration data with the best fit for the newly connected components.

15. The video endoscopic device according to claim 1, wherein the distal end of the endoscope shaft, the proximal end of the endoscope shaft and/or a light inlet of the camera head has at least one optically transparent protective window.

* * * * *